(12) United States Patent
Ishii et al.

(10) Patent No.: US 7,387,618 B2
(45) Date of Patent: *Jun. 17, 2008

(54) MEDICAL CONNECTOR AND METHOD FOR NASALLY ADMINISTERING OR REMOVING A SUBSTANCE

(75) Inventors: Jerry Seiichi Ishii, Mission Viejo, CA (US); Alison Diana Burcar, Laguna Beach, CA (US); Rita Bennett, San Clemente, CA (US)

(73) Assignee: ICU Medical, Inc., San Clemente, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 11/417,813

(22) Filed: May 3, 2006

(65) Prior Publication Data

US 2006/0197046 A1 Sep. 7, 2006

Related U.S. Application Data

(63) Continuation of application No. 10/444,497, filed on May 23, 2003, now Pat. No. 7,156,826.

(51) Int. Cl.
*A61M 5/00* (2006.01)
(52) U.S. Cl. ...................... 604/256; 604/523
(58) Field of Classification Search ................ 604/256, 604/523, 533–539, 284, 93.01, 95.02, 118, 604/264, 258, 94.01
See application file for complete search history.

(56) References Cited

U.S. PATENT DOCUMENTS

| | | | |
|---|---|---|---|
| 2,464,933 A | 3/1949 | Kaslow | |
| 2,705,955 A | 4/1955 | Nesset et al. | |
| 3,276,472 A | 10/1966 | Jinkens et al. | |

(Continued)

FOREIGN PATENT DOCUMENTS

DE 9100884 5/1992

(Continued)

OTHER PUBLICATIONS

International Search Report and Written Opinion dated Sep. 16, 2004.

(Continued)

*Primary Examiner*—Nicholas Lucchesi
*Assistant Examiner*—Laura A. Bouchelle
(74) *Attorney, Agent, or Firm*—Knobbe Martens Olson & Bear LLP

(57) ABSTRACT

A medical connector contains a plurality of arms having respective entrance ports. The medical connector also contains a cover preferably having first and second caps coupled together by a first tether, and a fastener coupled to at least one of the first and second caps by a second tether. The fastener is secured to a portion of the medical connector. The first and second caps are adapted to cover at least a portion of the entrance ports of respective first and second arms of the plurality of arms. The medical connector preferably has a sleeve that is detachably coupled to a first arm of the plurality of arms. The first cap preferably comprises a first portion with a first inner diameter adapted to encircle an end of the first arm and a second portion with a second inner diameter adapted to encircle a distal end of the sleeve.

9 Claims, 7 Drawing Sheets

U.S. PATENT DOCUMENTS

| | | | |
|---|---|---|---|
| 4,349,024 A * | 9/1982 | Ralston, Jr. | 604/403 |
| 4,390,017 A | 6/1983 | Harrison et al. | |
| 4,410,320 A | 10/1983 | Dykstra et al. | |
| 4,580,556 A | 4/1986 | Kondur | |
| 4,661,110 A * | 4/1987 | Fortier et al. | 604/256 |
| 4,790,832 A * | 12/1988 | Lopez | 604/523 |
| 4,798,592 A | 1/1989 | Parks | |
| 4,842,591 A | 6/1989 | Luther | |
| 4,895,562 A | 1/1990 | Lopez | |
| 5,071,405 A | 12/1991 | Piontek et al. | |
| 5,144,972 A | 9/1992 | Dryden | |
| 5,342,326 A | 8/1994 | Peppel et al. | |
| 5,382,242 A | 1/1995 | Horton et al. | |
| 5,385,372 A | 1/1995 | Utterberg | |
| 5,445,630 A | 8/1995 | Richmond | |
| 5,674,209 A | 10/1997 | Yarger | |
| 5,749,097 A | 5/1998 | Garrett-Roe | |
| 5,755,702 A | 5/1998 | Hillstead et al. | |
| 5,919,170 A | 7/1999 | Woessner | |
| 6,068,617 A | 5/2000 | Richmond | |
| 6,409,220 B1 | 6/2002 | Wing et al. | |
| 6,460,560 B1 | 10/2002 | Fawcett et al. | |
| 7,156,826 B2 * | 1/2007 | Ishii et al. | 604/256 |
| 2003/0163119 A1 | 8/2003 | Chu et al. | |

FOREIGN PATENT DOCUMENTS

| | | |
|---|---|---|
| WO | WO 90/05556 | 5/1990 |
| WO | WO 03/101519 | 12/2003 |
| WO | WO 2004/105857 A1 | 12/2004 |

OTHER PUBLICATIONS

International Preliminary Report dated Dec. 8, 2005.
U.S. Appl. No. 10/444,497, filed May 23, 2003, pending.
U.S. Appl. No. 11/418,500, filed May 3, 2006, pending.

* cited by examiner

MEDICAL CONNECTOR AND METHOD FOR NASALLY ADMINISTERING OR REMOVING A SUBSTANCE

CROSS-REFERENCE TO RELATED APPLICATION

This application is a continuation of U.S. application Ser. No. 10/444,497, filed May 23, 2003, now U.S. Pat. No. 7,156,826, which is incorporated by reference in its entirety.

BACKGROUND OF THE INVENTION

1. Field of the Invention

The present invention is directed to medical connectors, and more specifically, to a medical connector for nasally administering or removing a substance from a patient's stomach.

2. Description of the Related Art

When a patient cannot receive medication and food orally, a nasal gastric tube may be employed for introducing medication and food into the stomach. Nasal gastric tubes may also be used for withdrawing substances from a patient's stomach. Such tubes comprise a flexible plastic material which comes in various diameters depending upon the size of the patient and the nature of the substance to be passed through the tube. The tube is fed through the patient's nose, down the esophagus and into the patient's stomach, while taking care not to insert the tube into the patient's lungs. A portion of the tube extends out of the patient's nostril and terminates at a point remote therefrom.

U.S. Pat. No. 4,895,562 to Lopez, which is incorporated herein by reference, discloses a medical connector for attachment to the end of a nasal gastric tube. The medical connector comprises three passageways having entrance and exit ports. A stop-cock type valve is disposed at the convergence of the passageways such that different combinations of the passageways may be connected in fluid communication. Various types of medical devices may be attached to the medical connector, such as syringes, syringe pumps, and/or collection bags, for administering or removing substances to or from the patient's stomach.

For example, in one embodiment disclosed in the '562 patent, the first passageway is in fluid communication with a syringe pump for administering or removing a substance to or from the patient's stomach, the second passageway is in fluid communication with a syringe for applying medication, and the third passageway is in fluid communication with the nasal gastric tube. In a first valve position, the second and third passageways are in fluid communication so as to allow the flow of substances into the patient. The syringe connected to the second passageway may contain medication or wash-out fluid for cleaning toxic contaminants from the patient's stomach. In a second position, the passageway to the syringe is blocked and the first and third passageways are in fluid communication so that food may be pumped into the patient or substances may be pumped from the patient's stomach.

In the course of such medical procedures, one or more of the components of the stomach-pumping system may be temporarily detached. During these periods of detachment, there is a risk of contamination of the medical connector from outside sources and/or a risk that the contents of the connector may drip out and contaminate other devices or persons. A patient undergoing nasal administration of food or medication may be especially susceptible to infection, and care must be taken to maintain devices in contact with the patient as sterile as possible. Moreover, substances that must be removed from a patient's stomach generally have inherently dangerous chemical or biological properties and could cause harm to others after they are withdrawn. Thus, there is a need for a medical connector in a stomach-pumping system with openings that can be conveniently and repeatedly sealed off during periods of detachment from other components.

SUMMARY OF THE INVENTION

One aspect of the present invention involves a medical connector comprising a plurality of arms and a cover. Each of the plurality of arms preferably has an entrance port coupled to a passageway. The passageways preferably converge at a valve. The valve may comprise a face with markings to indicate which of the passageways are in fluid communication. The markings are preferably black. The cover preferably comprises first and second caps, first and second tethers, and a fastener. The first and second caps are preferably coupled together by the first tether. The second tether and the fastener preferably couple the cover to the medical connector.

The first cap is adapted to cover at least a portion of the entrance port of the first arm and the second cap is adapted to cover at least a portion of the entrance port of the second arm. At least one of the caps preferably comprises a first portion with a first inner diameter adapted to encircle an end of an arm of the medical connector and a second portion with a second inner diameter adapted to encircle a region on the arm adjacent to the end. Alternatively, a sleeve may be coupled to the end of an arm and the cap may be configured to cover an open end of the sleeve.

A method of using the medical connector preferably comprises: (1) inserting a tube through a nostril of a patient; (2) coupling a medical connector, made in accordance with an embodiment of the invention, to the tube; (3) removing the first and/or second caps from the first and second arms; (4) connecting a first medical device to the first arm and/or a second medical device to the second arm; (5) adjusting a valve of the medical connector so as to allow a substance to flow between the stomach and the first medical device; and (6) disconnecting either or both medical devices and re-attaching one or both caps to the arms of the medical connector.

BRIEF DESCRIPTION OF THE DRAWINGS

The foregoing features, aspects, and advantages of the present invention will now be described with reference to the drawings of preferred embodiments that are intended to illustrate and not to limit the invention.

DETAILED DESCRIPTION OF THE PREFERRED EMBODIMENTS

The following detailed description of preferred embodiments refers to the attached figures; however, the invention is not limited to any particular embodiment(s) disclosed herein. The scope of the present invention is intended to be defined only by reference to the appended claims.

Figure 2:
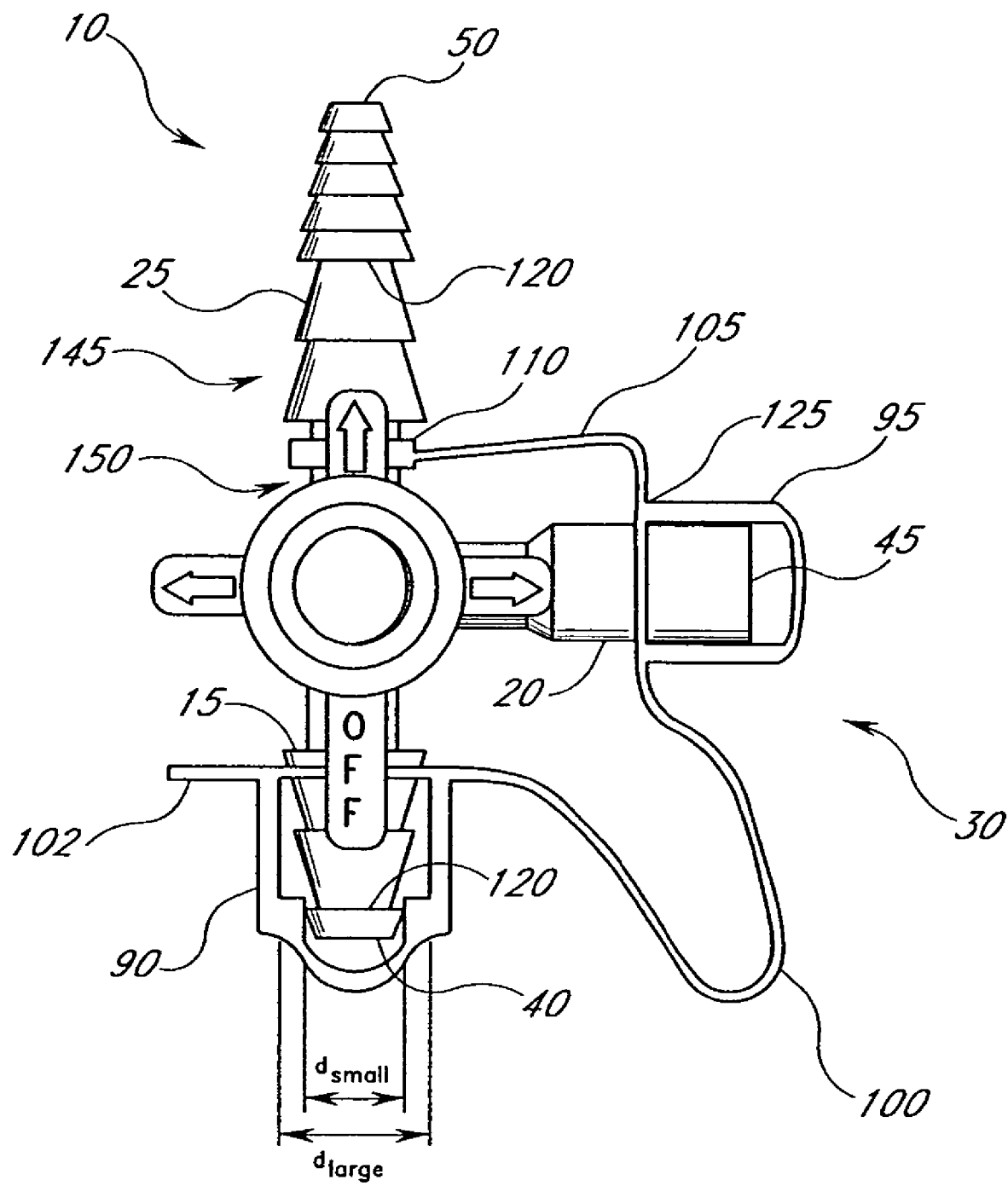
FIG. 2 is an enlarged schematic illustration of a medical connector of FIG. 1.
Figure 3:
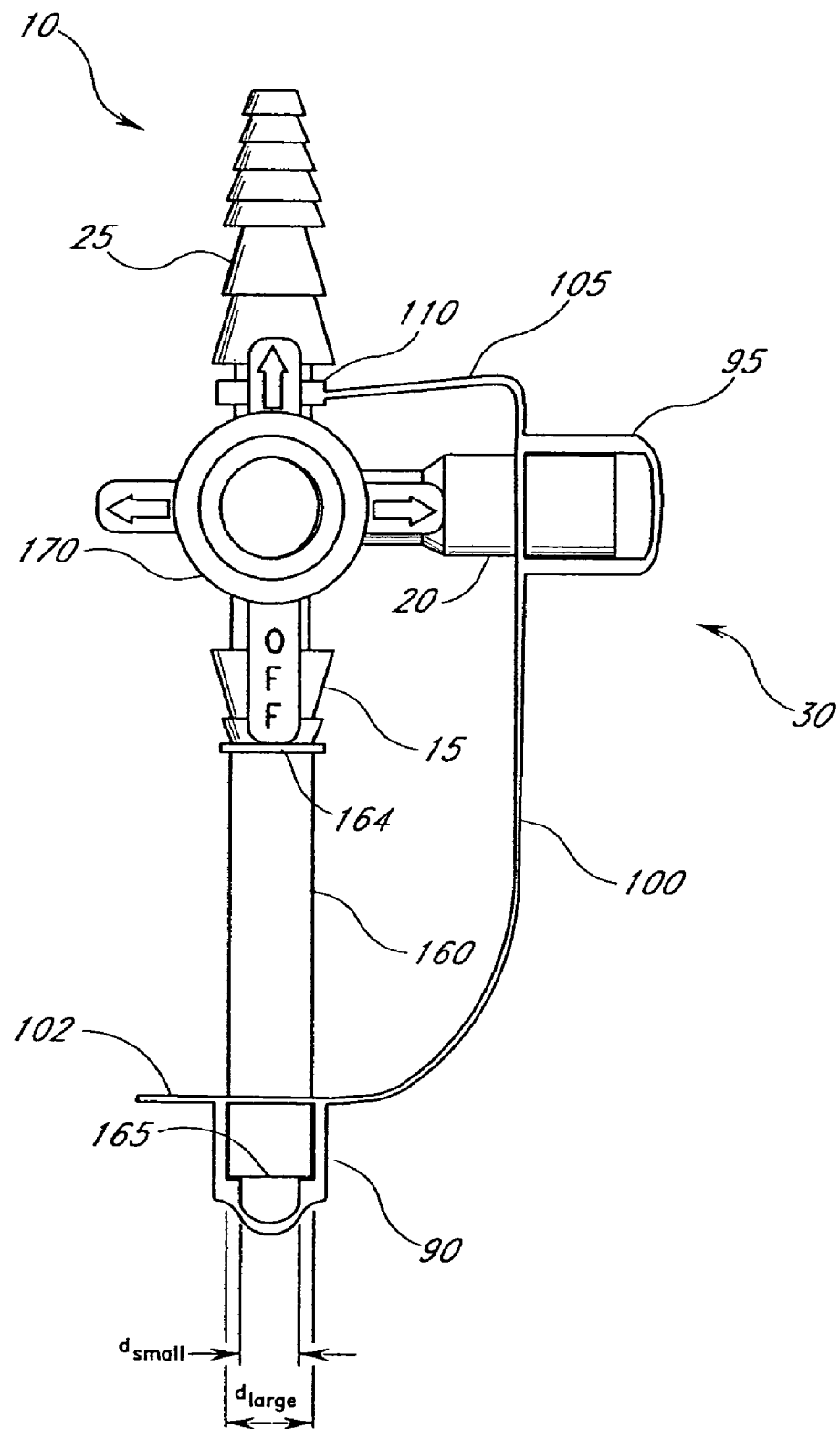
FIG. 3 is a schematic illustration of an embodiment of a medical connector according to the present invention including a sleeve.
Figure 4:
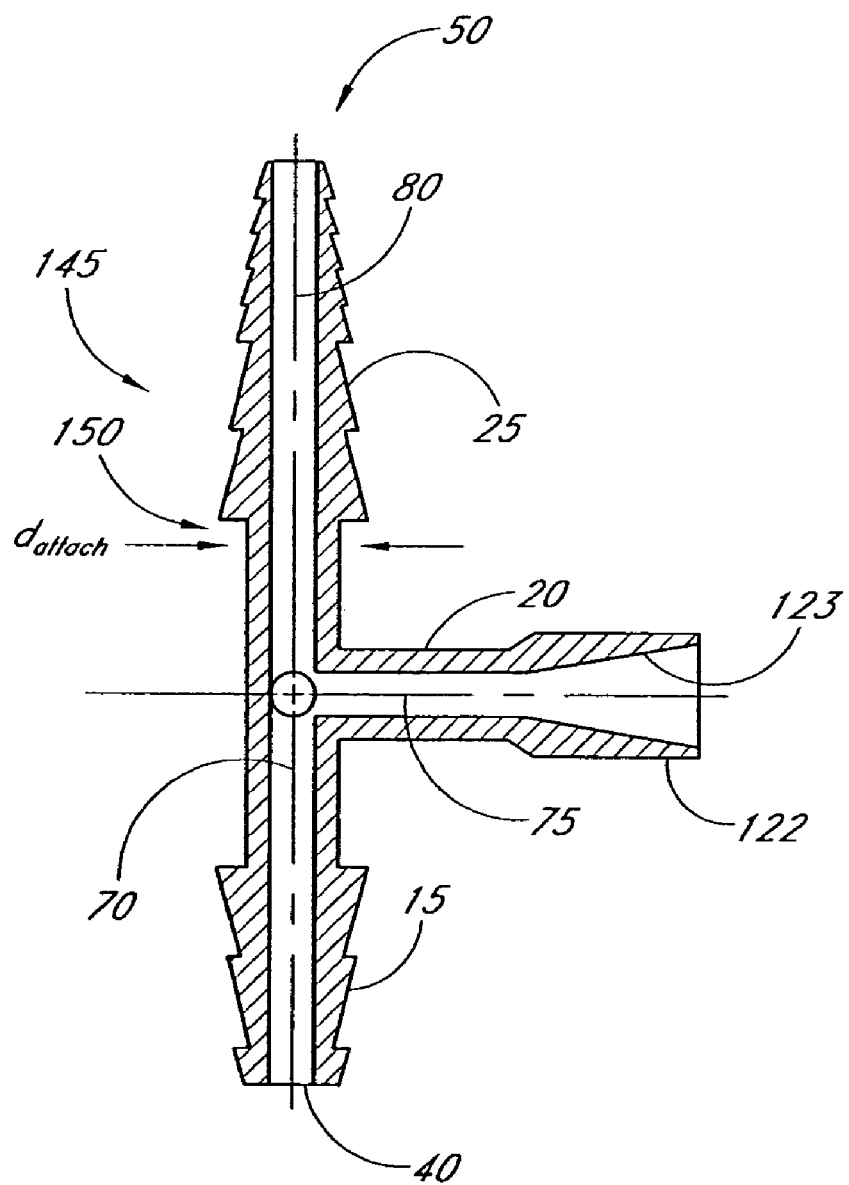
FIG. 4 is a cross-section view of the medical connector in FIG. 2 wherein the valve and the cover are not shown.
Figure 5:
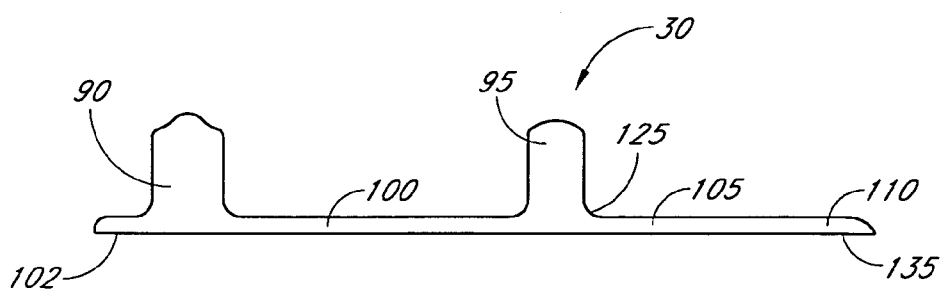
FIG. 5 is a side view of an alternative embodiment of a cover in accordance with the present invention.

In certain embodiments, such as that schematically illustrated in FIGS. 1-4, a medical connector 10 comprises a plurality of arms (e.g., a first arm 15, a second arm 20, and a third arm 25) and a cover 30. The plurality of arms 15, 20, 25 each has corresponding entrance ports 40, 45, 50 (FIG. 2) coupled to corresponding passageways 70, 75, 80 (FIG. 4).

The cover 30 preferably comprises a first cap 90, a second cap 95, a first tether 100, a second tether 105, and a fastener 110. The first cap 90 and second cap 95 are preferably coupled together by the first tether 100. The fastener 110 is secured to a portion of the medical connector 10 and coupled to at least one of the first and second caps 90, 95, preferably by a second tether 105. The first cap 90 is adapted to cover at least a portion, and preferably all, of the first entrance port 40 of the first arm 15 and the second cap 95 is adapted to cover at least a portion, and preferably all, of the second entrance port 45 of the second arm 20.

As used herein, the term "entrance port", when applied to the arms 15, 20, 25 of the medical connector 10, means the opening at the end of each arm in communication with the environment. The entrance port of an arm is generally where a tube, syringe, or other component external to the medical connector 10 may be placed in fluid communication with the connector 10. The term "entrance port" does not imply that a substance must flow through the medical connector 10 in a specific direction.

As shown in FIG. 2, at least one of the plurality of arms 15, 20, 25 preferably comprises a series of different sized tapered flanges 120 that are adapted to receive tubes of different diameters. The flanges 120 near the entrance ports 40, 50 have a smaller diameter, while the flanges 120 further from the entrance ports 40, 50 have a larger diameter, and the flanges in between increase in diameter incrementally from each end. The flanges of increasing diameter facilitate creating a secure interference fit between an end of an arm and another component such as a tube.

In certain embodiments, at least one of the plurality of passageways 70, 75, 80 is tapered. For instance, in the illustrated embodiment of FIG. 4, the second arm 20 is configured such that the passageway 75 has an inwardly tapering sidewall 123 that approximately matches the taper of the luer of a syringe. The inwardly tapering sidewall 123 is adapted such that the luer fits snugly within the passageway 75. In other embodiments, the inwardly tapering sidewall 123 may be adapted to receive and secure a mating fitting of a syringe pump. In yet other embodiments, the second arm 20 may be configured to provide a secure connection with a medical implement, such as a syringe, using a luer lock. In such an embodiment, the end of the second arm 20 preferably includes threads, rabbit ends, or any other suitable securing means. The description of such fittings and connections on the second arm 20 is exemplary and it will be appreciated that one or more of the other arms 15, 25 may include any one of a variety of such fittings and/or connections.

Although the medical connector 10 illustrated in FIGS. 1-4 comprises three arms 15, 20, 25, other embodiments may have more or fewer arms. The cover 30 may be configured, as necessary, with fewer or additional caps similar to the first and second caps 90, 95, and fewer or additional tethers for preferably coupling the caps together into a single cover 30.

As illustrated in FIG. 3, the medical connector 10 may further comprise a sleeve 160 detachably coupled to the first arm 15. The sleeve 160 has a proximal end 164 and a distal end 165, and may be constructed to be a universal adapter for receiving tubes of different diameters. For example, the inside of the sleeve 160 may be fabricated of a resilient material, such as a silicon rubber, that expands to accommodate cannulas of varying diameters on medical devices such as syringes or syringe pumps. The inner diameter of the sleeve 160 may comprise one or more taper profiles that increase the range of tube diameters that may be received and securely held by the sleeve 160.

The length of the sleeve 160 is selected to achieve certain design objectives. If the sleeve 160 is too long, the distal end 165 of the sleeve 160 may interfere with medical procedures in which the medical connector 10 is used or may cause discomfort to the patient. Preferably, the length of the sleeve 160 is between about ½ inches and about 3 inches, even more preferably between about 1 inch and about 2½, and most preferably about 1½ inches; however, sleeves having lengths outside these ranges are also consistent with embodiments of the medical connector 10 and the cover 30.

Referring to FIGS. 5-8, the cover 30 preferably comprises first and second caps 90, 95, which are preferably coupled together by the first tether 100. The first cap 90 is adapted to cover at least a portion of a first arm 15 and the second cap is adapted to cover at least a portion of the second arm 20. Fastener 110 is preferably coupled to at least one of the first and/or second caps 90, 95, or the first tether 100 by the second tether 105.

In certain embodiments, the first cap 90 may be used to cover either the distal end 165 of the sleeve 160 (FIG. 3) or the end of the arm 15 when the sleeve 160 is not attached to the first arm 15 (FIG. 2).

Figure 7:
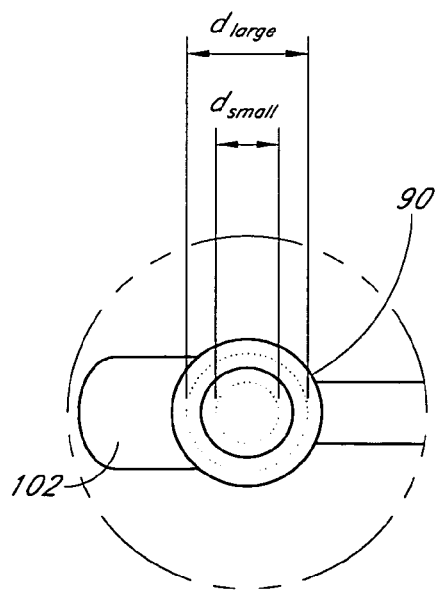
FIG. 7 is a magnified top view of a cap shown in FIG. 6.

As illustrated in FIG. 7, the first cap 90 preferably comprises a first portion characterized by a first inner diameter $d_{small}$, that is adapted to encircle an end of the first arm 15 and a second portion with a second inner diameter $d_{large}$ that is adapted to encircle the distal end 155 of the sleeve 160. The smaller-diameter portion is preferably at the end of the cap (see, e.g., FIG. 2), and forms a dome-like structure above the larger-diameter portion.

The use of a cap having two diameters $d_{small}$, $d_{large}$ offers many advantages. For example, it allows a single cap, such as the cap 90, to be used whether or not a larger-diameter sleeve 160 is attached to the first arm 15. It obviates the need of providing a separate, third cap or some other means to cover the sleeve 160. The two diameters of the first cap 90 also allow a single cap to fit multiple arms of the medical connector 10 having different diameters. The cover 30 could comprise a single cap 90 that fits both the first arm 15 (using the diameter $d_{small}$) and the second arm 20 (using the diameter $d_{large}$). Alternatively, the cover 30 depicted in FIGS. 5 and 6 could be used on a medical connector 10 having more than three arms. The cap also may be configured with three or more sections of different diameters to accommodate an even wider range of diameters of arms and/or sleeves.

The second cap 95 may be configured similarly to the first cap 90, such that the second cap 95 has portions characterized by a smaller diameter and a larger diameter. Alternatively, the first and/or second diameters of the second cap 95, may be different from those used for the first cap 90.

In other embodiments, the cover 30 may comprise a single cap 90 having two diameters $d_{small}$, $d_{large}$. In such embodiments, the cap 90 may be constructed so that it is not tethered to the medical connector 10, in which case it may be placed or stored in an appropriate location when the first cap 90 is removed from the medical connector 10. Alternatively, the cover 30 may comprise a single cap 90, a fastener 10, and a tether 100 for coupling the cap 90 and the fastener 110 together. The fastener is coupled to a portion, preferably an arm, of a medical connector. Whether or not the single cap 90 is attached to a fastener 110, the smaller diameter of the cap 90 may be used to cover the end of an arm of the medical connector 10 and the larger diameter may be used to cover the end of a different arm of the medical connector 10 or a sleeve 160, if attached.

Two or more covers may also be applied to a single medical connector 10, each cover having one or more caps for covering the ports on different arms of the medical connector 10. One or more of the covers may optionally comprise its own fastener, such as the fastener 110, for securing the covers to the medical connector 10. Alternatively, a single fastener 110 may be couple to a plurality of tethers that are connected to each of the caps used on the medical connector 10.

The caps 90, 95 of the cover 30 may be used to cover the entrance ports 40, 45 prior to use of the medical connector 10 and during periods when the first and second arms 15, 20 are disconnected from medical devices. The caps 90, 95 are preferably made of a flexible material, such as a medically inert plastic, and thus stretch during attachment to the arms 15, 20, providing a tight seal around the entrance ports 40, 45. Alternatively, the first cap 90, the second cap 95, or both may be made of a rigid material such as a hard plastic or metal. In this case, the caps 90, 95 are preferably constructed so as to snap or screw onto the ends of the first and second arms 15, 20, to form a tight seal around the entrance ports 40, 45.

In certain embodiments, only the first cap 90 is tightly secured to the arm 15, while the second cap 95 more loosely surrounds the end of the second arm 20. In such embodiments, the first tether is stretched during attachment of the first cap 90 and the tension of the tether holds the second cap 95 in place over the end of the second arm 20. When the first cap 90 is removed from the first arm 15, the second cap is easily removed, allowing both entrance ports 40, 45 to be quickly uncovered and made available for use.

The second tether 105 is preferably affixed to an edge 125 of the second cap 95 such that the second cap 95 and the second tether 105 are disposed in a substantially common plane on a bottom side 130 of the cover 30 when the cover 30 is laid flat. Other attachment locations and orientations of the second tether 105 may also be used. For instance, the second tether 105 may be secured to the first cap 90, or to the first tether 100, or to a different location. The second tether 105 may alternatively be secured at a different angle or to a different portion of the cap to facilitate attachment to the arms.

The primary advantage of the tethers 100, 105 is to keep the first and second caps 90, 95 in proximity to their respective first and second arms 15, 20 when the caps are not covering the entrance ports 40, 45 (for example, when they are removed so that medical devices may be connected to the arms). This keeps the caps 90, 95 from being lost or contaminated, or from releasing contaminated material. By keeping the caps 90, 95 in close proximity to the medical connector 10, the caps 90, 95 are also readily available to quickly cover the entrance ports 40, 45, to prevent backwash and contamination problems when the medical devices are removed. The tethers also permit one-handed opening or closing of the passages. Caps without tethers would require one hand for holding the medical connector 10 and another hand to remove, or re-attached, and hold the cap. Medical practitioners are often required to hold multiple implements during medical procedures and the one-handed attachment and removal of the caps is therefore a significant advantage.

When the first cap 90 is disconnected, it may be desirable in certain cases that the first cap 90 remains particularly close to medical valve 10. This natural disposition of the first cap 90 closer to the entrance port 40 helps to prevent the cover 30 from interfering with medical procedures preformed and also reduces the amount of annoyance experienced by the patient from the cap 90 dangling farther from the medical connector 10.

Figure 9:
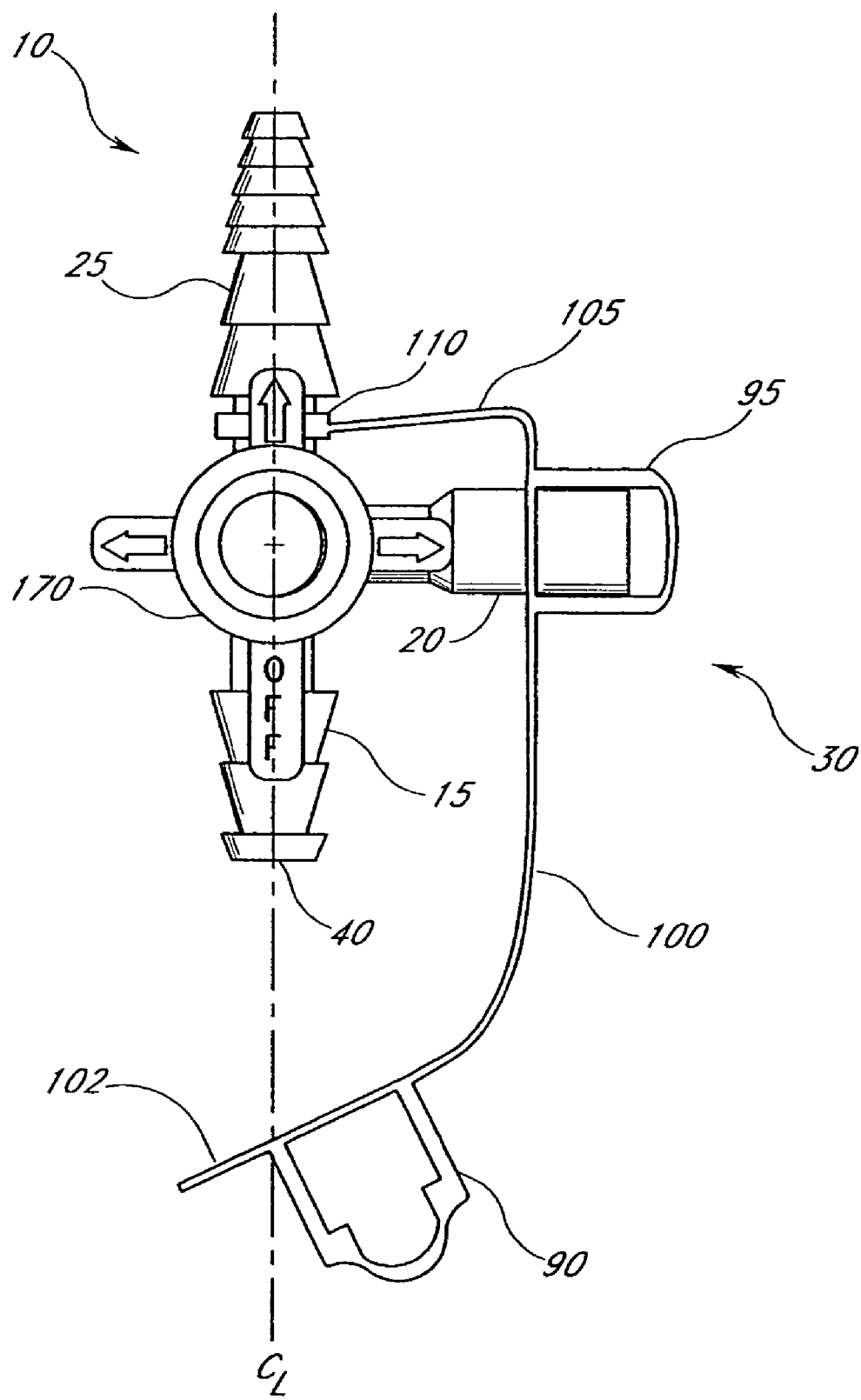
FIG. 9 is a schematic illustration of a medical connector according to an embodiment of the present invention with one of two caps removed from its respective arm.

FIG. 9 illustrates one embodiment of the cover 30 wherein the first cap 90 remains relatively near the medical valve 10. In such an embodiment, at least one of the first and second tethers 100, 105 is structured so that first cap 90 is disposed close to a center line CL passing through the center of the first arm 15 when the first cap 90 is removed from the first arm 15.

Figure 8:
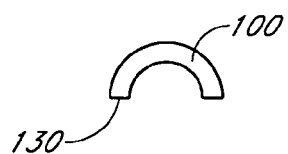
FIG. 8 is a cross-sectional view of a tether of the cover of FIG. 6 along the line 8-8.

FIG. 8 illustrates one configuration of the first and second tethers 100, 105 for providing such a natural disposition of the first cap 90, wherein at least one of the first and second tethers 100, 105 has a substantially u-shaped cross-section. The u-shaped cross-section of the tethers 100, 105 creates a biasing condition in which the tether has a natural tendency to bend inwardly toward the entrance port 40.

Preferably, the fastener 110 is secured to one of the plurality of arms 15, 20, 25. As shown in the illustrated embodiment of FIG. 2, the fastener 110 is secured to the third arm 25; however, the fastener 110 may alternatively be secured to another arm of the medical connector 10, such as the second arm 20, or to some other portion of the medical connector 10.

Figure 6:
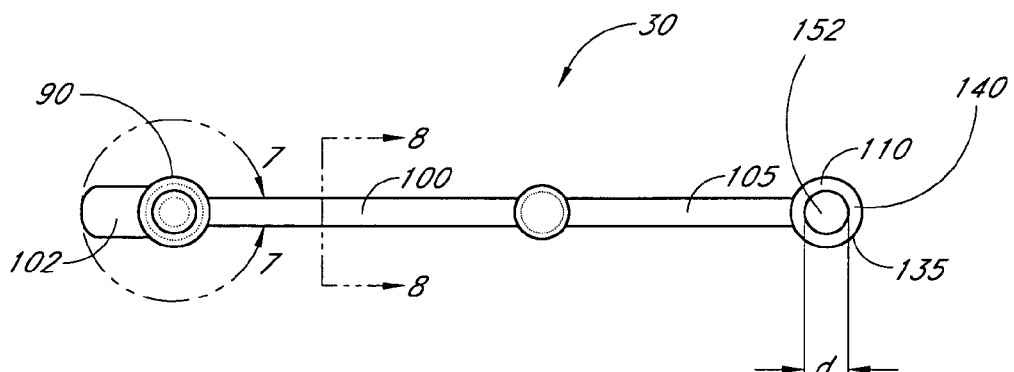
FIG. 6 is a top view of the cover shown in FIG. 5.

As illustrated in FIG. 6, the fastener 110 preferably comprises a ring 140 with an inner diameter d. The arm to which the fastener 110 attaches may comprise a body portion 145 and a neck portion 150, wherein the neck portion 150 has an outer diameter $d_{attach}$ (see FIG. 4). In certain embodiments, the inner diameter d of the fastener 110 is substantially equal to the neck diameter $d_{attach}$. In other embodiments, the inner diameter d of the ring 140 is larger than the diameter $d_{attach}$, allowing the cover 30 to freely rotate about and slide along the neck portion 150. For example, in one embodiment the neck portion 150 has a diameter $d_{attach}$ that is approximately ¼ inch and the inner diameter d is approximately ¹⁄₃₂ to ¹⁄₁₆ inch larger that the diameter $d_{attach}$.

The fastener 110 may also comprise a resilient material, and the inner diameter d of the fastener 110 may, prior to attachment of the fastener 110, be less than the neck diameter $d_{attach}$. In such an embodiment, the ring 140 is pressed or stretched over one of the plurality of arms 15, 20, 25.

A fastener may alternatively comprise a void that is non-circular and, therefore, is not characterized by a single diameter d. For instance, the void may comprise a hexagonal or octagonal shape that has favorable manufacturing characteristics. If the medical connector and one or more of the tethers are integrally formed, the fastener(s) would constitute the juncture(s) between such tether(s) and the body of the medical connector.

For simplicity during fabrication, in certain embodiments, the first and second tethers 100, 105, the first and second caps 90, 95, and fastener 110 may be integrally formed using a common mold. In other embodiments, one or more of these components of the cover 30 are separately constructed and then attached to the remaining components. For example, the fastener 110 may be made separately from the other components of the cover 30 and from a more durable material. If the fastener 110 is made from a more durable material, it will accommodate a higher stress loading during use of the medical connector 10. The rest of the components of the cover 30, which might experience less stress during use, could be made of a material having other desirable characteristics, such as lower cost or greater elasticity.

Figure 10:
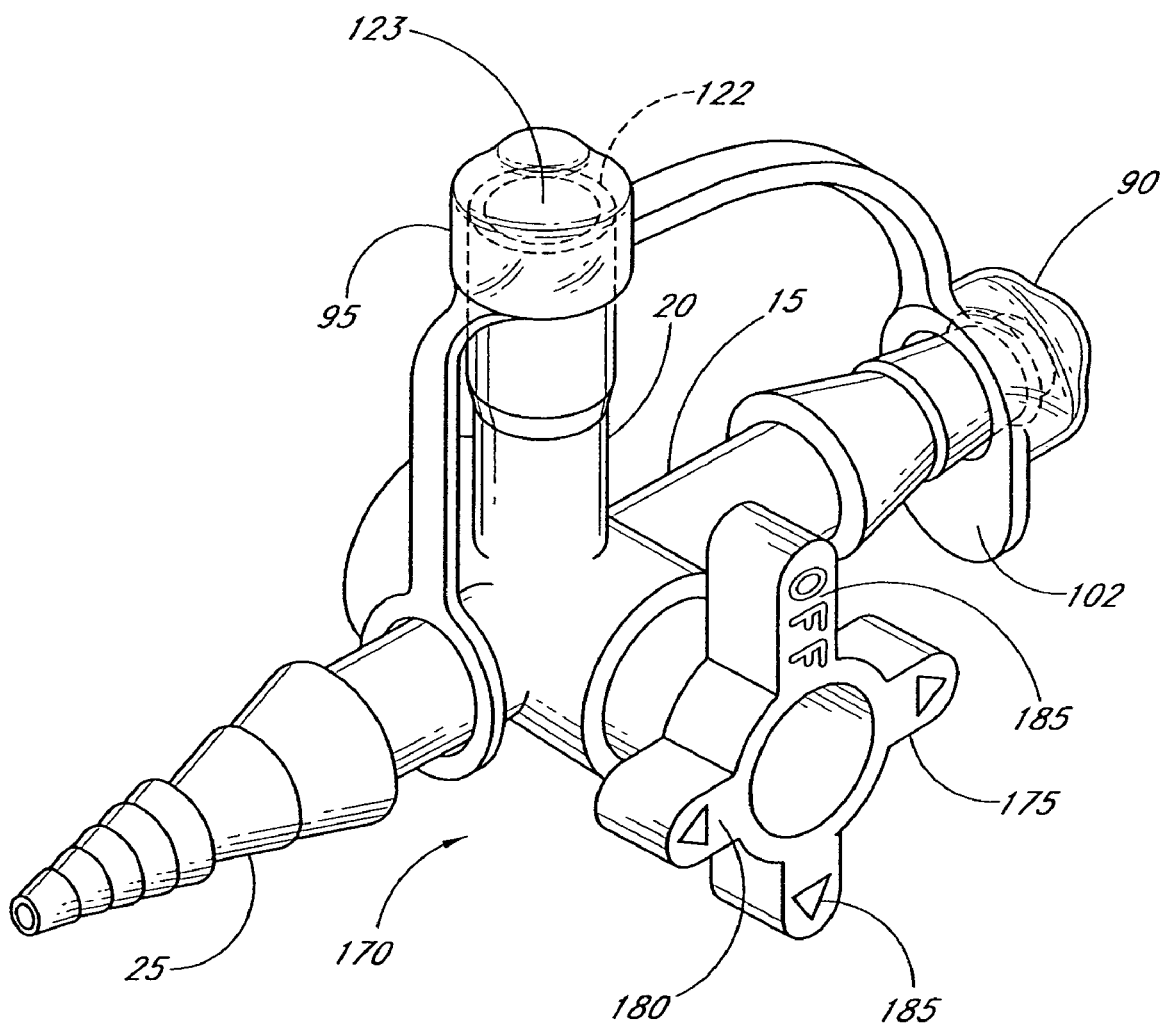
FIG. 10 is a perspective view of an embodiment of a medical connector according to the present invention.

Referring to FIG. 10, the medical connector 10 preferably comprises a valve 170 that is adapted to selectively connect two or more of the plurality of passageways 70, 75, 80 of the arms 15, 20, 25. The valve 170 may have a handle 175 that is rotated to different positions to connect the various passageways 70, 75, 80. In certain embodiments, the handle 175 comprises a face 180 with markings 185 that are adapted to indicate which of the passageways 70, 75, 80 are in fluid communication. The markings 185 preferably comprise a set of three arrow and the word "OFF".

Preferably, the face 180 has a surface that is white and diffuses light, so as to provide a contrast to the markings 185. In one embodiment, the markings 185 are red in color. In a preferred embodiment, the markings 185 are black in color. The use of black markings is believed to provide better wear characteristics in connection with the visibility of the markings 185 after prolonged periods of use of the medical connector 10. In yet other embodiments, the markings 185 may comprise a phosphorescent paint that is visible under low lighting conditions.

Figure 1:
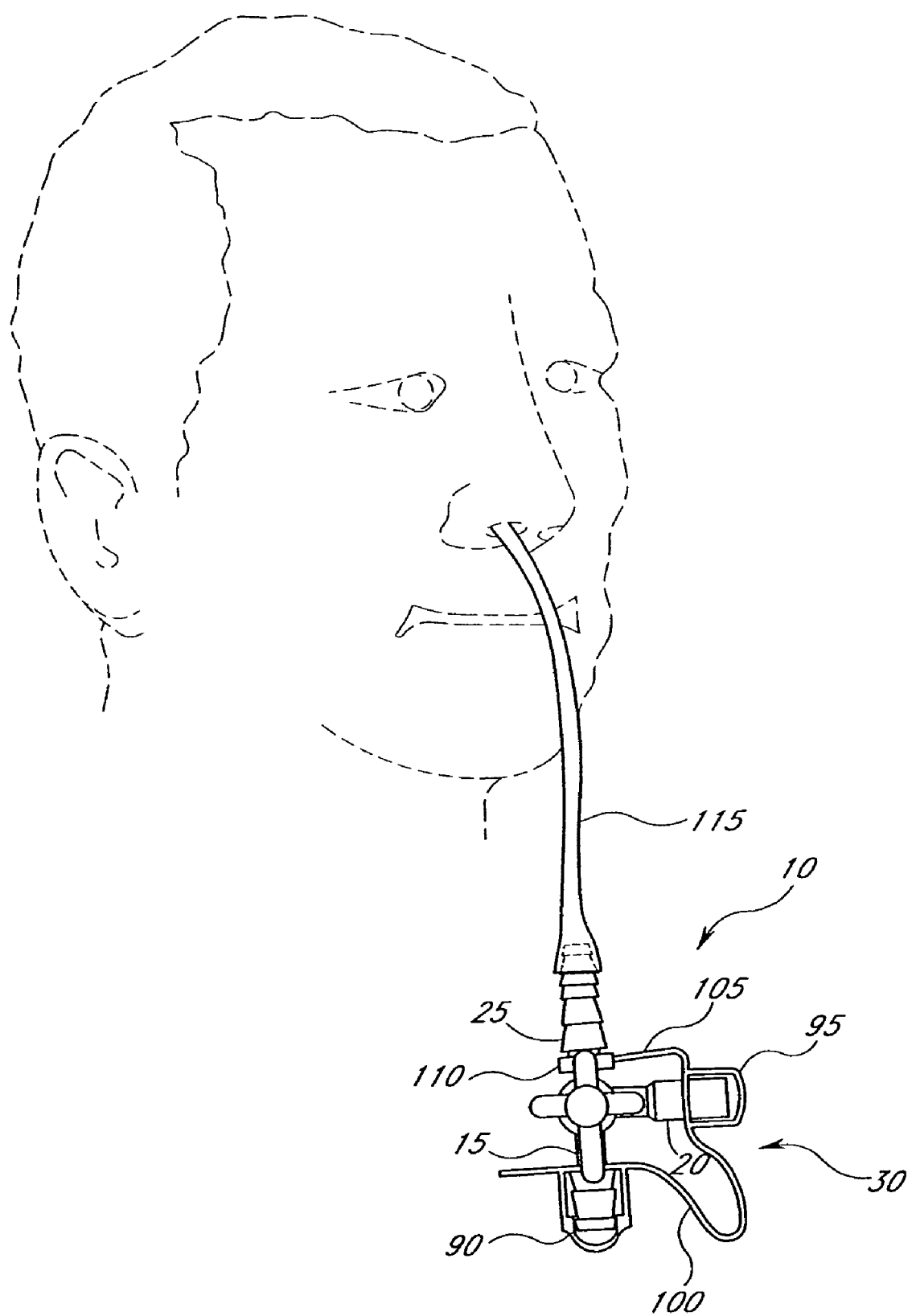
FIG. 1 is a schematic illustration of a medical connector according to an embodiment of the present invention wherein an arm of the connector is attached to a tube having one end disposed inside a patient's stomach.

Before use, the medical connector 10 is preferably pre-packaged inside a sealed, sterile container with the first and second caps 90, 95 attached to the first and second arms 15, 20 so as to cover the first and second entrance ports 40, 45. Once removed from the container, the medical connector 10 may be attached to tube 115 as illustrated in FIG. 1, that is with the caps 90, 95 still attached to the first and second arms 15, 20. The tube 115 may be made of a resilient material, such as Tygon® and the first arm 15 may comprise a series of different-sized tapered flanges 120 to aid in attaching the tube 115.

One method of using the medical connector 10 comprises the steps of: removing the first and second caps 90, 95 from the first and second arms 15, 20; connecting a first medical device to the first arm and/or a second medical device to the second arm; adjusting the valve 170 so as to allow a substance to flow between the stomach and the first medical device; and disconnecting either or both medical devices and attaching one or both caps 90, 95 to the arms 15, 20 of the medical connector 10.

If only one medical devices is attached to the medical connector 10, the medical practitioner need only remove one of the caps 90, 95. The remaining cap may be removed at a later time, as necessary, when the second medical device is ready for attachment to the medical connector 10.

At least one of the caps 90, 95 preferably comprises a tab 102. The tab may be disposed, for example, on the side of the cap opposite from the point of connection to the tether 100. The tab 102 is used as an aid in removing the first and second caps 90, 95. The tab 102 is preferably pushed away from the medical connector 10 with the thumb, while simultaneously gripping the medical connector with the same hand. In certain embodiments, the u-shape of the first tether 100 or some other means causes the first cap 90 to remain relatively close to the first entrance port 40. Once the first cap 90 is removed from the first arm 15, the cap 90 may be positioned as necessary to allow a medical device to be attached to the medical connector 10. The second cap 95 may subsequently be removed by pulling on the cap 90 and/or the first tether 100. If the first and second tethers 100, 105 are made of a resilient material, the second cap 95 can alternatively be removed prior to removing the first cap 90 by gripping and pulling the second cap 95 away from the medical connector 10. This causes the first and second tethers 100, 105 to be stretched until the second cap 95 is pulled over the end of the second arm 20.

A first medical device is connected to the first arm and/or a second medical device is connected to the second arm after the selected caps 90, 95 have been removed. Various types of medical devices may be attached to the first and second arms 15, 20. For instance, the second arm 20 may be connected first to a syringe containing a medication or a cleansing solution for injection into the stomach through the tube 115. Once the medication and/or cleansing fluid has been so injected, the syringe may be removed from the second arm 20 and replaced with a syringe pump to withdraw the content of the patient's stomach, including the medication and/or cleansing fluid. After the substance in the stomach is removed using the syringe pump, the handle 175 of the valve 170 may be rotated approximately 90 degrees counterclockwise from the position shown in FIG. 10, so as to put the passages 70, 75 in fluid communication. The syringe pump may then be used to transfer the substance from the syringe pump into a container attached to the first arm 15. Once the substance is transferred the container, the container may be detached from the medical valve and the substance removed. The first arm 15 may be connected to a container such as an expandable bag for receiving a substance from the stomach that may be injected using the syringe pump attached to the second arm 20.

In one embodiment, the step of adjusting the valve 170 comprises rotating the handle 175 to one or more positions so as to allow a plurality of the passages 70, 75, 80 to be in fluid communication. The valve 170 interconnects the passageways 70, 75, 80 depending upon which of the arms 15, 20, 25 are aligned to the arrowheads on the face 180 of the valve 170. When the word "OFF" is aligned to one of the arms 15, 20, 25, the passageway corresponding to that arm is turned off and is isolated from the passageways of the remaining arms.

For example, in the illustrative embodiment shown in FIG. 10, the word "OFF" is aligned to the second arm 20 and two of the arrows are aligned to the first and third arms 15, 25. In this orientation of the valve 170, the first and third passageways 70, 80 (see FIG. 4) of the first and third arms 15, 25 are in fluid communication and the second passageway 75 of the second arm 20 is isolated. Thus, substances such as medication, cleansing fluid, or contents of the stomach of a patient may flow between the tubes connected to the first and third arms 15, 25.

If the valve 170 is rotated 90 degrees clockwise from the position shown in FIG. 10, as viewed from the front face 180, the first passageway 70 of the first arm 15 is turned off and the second and third passageways 75, 80 of the second and third arms 20, 25 are in fluid communication. Conversely, if the valve 170 is rotated 90 degrees counterclockwise from the position shown in FIG. 10, as viewed from the front face 180, the third passageway 80 of the third arm 25 is turned off and the first and second passageways 70, 75 of the first and second arms 15, 20 are in fluid communication. If the valve 170 is rotated 180 degrees from the position shown in FIG. 10, all three passageways 70, 75, 80 of the three arms 15, 20, 25 are all interconnected and in fluid communication.

In certain embodiments, if the valve 170 is rotated approximately ±45 degrees or ±135 degrees from the position shown in FIG. 10, each of the passageways 70, 75, 80 are isolated and are not in fluid communication with any of the other passageways 70, 75, 80. In this position, essentially no fluid or other substance flows through the valve 170.

The method of using the medical connector 10 also preferably comprises a step of disconnecting either or both medical devices sometime during the medical procedure. When a medical device is disconnected, one or both caps 90, 95 are re-attached to the arms 15, 20 of the medical connector 10. In this way, the passageways 70, 75 of the medical connector 10 are isolated from the environment.

What is claimed is:

1. A medical connector, comprising:
    a plurality of arms;
    a first cap and a second cap directly coupled together by a first tether, the first cap adapted to substantially obstruct fluid flow through a first arm of the plurality of arms, the second cap adapted to substantially obstruct fluid flow through a second arm of the plurality of arms;
    a fastener secured to a portion of the medical connector and coupled to either the first cap or the second cap by a second tether, wherein the second tether is different than the first tether and the first cap is further adapted to remain in close proximity to the first arm when the first cap is not engaged with the first arm and the second cap is engaged with the second arm; and
    a valve adapted to selectively place two or more passageways in fluid communication.

2. The medical connector of claim 1, wherein the first cap further comprises a first portion with a first inner diameter adapted to encircle an end of the first arm and a second portion with a second inner diameter adapted to encircle a region near the end of the first arm.

3. The medical connector of claim 2, wherein the second cap further comprises a first portion with a first inner diameter adapted to encircle an end of the second arm and a second portion with a second inner diameter adapted to encircle a region near the end of the second arm.

4. The medical connector of claim 1, wherein the first cap further comprises a tab adapted to facilitate removal or attachment of the first cap to the first arm.

5. The medical connector of claim 1, wherein the fastener is secured to one of the plurality of arms.

6. The medical connector of claim 5, wherein the arm to which the fastener is secured is a third arm.

7. The medical connector of claim 5, wherein:
    the arm to which the fastener is secured comprises a body portion and a neck portion;
    the fastener comprises a ring with an inner diameter; and
    the inner diameter is less than a diameter of the body portion and is substantially equal to a diameter of the neck portion.

8. The medical connector of claim 1, further comprising a sleeve detachably coupled to the first arm.

9. The medical connector of claim 8, wherein the first cap is adapted to cover either the end of the first arm or the end of the sleeve.

* * * * *

UNITED STATES PATENT AND TRADEMARK OFFICE
CERTIFICATE OF CORRECTION

PATENT NO.         : 7,387,618 B2                                              Page 1 of 1
APPLICATION NO.    : 11/417813
DATED              : June 17, 2008
INVENTOR(S)        : Jerry Seiichi Ishii, Alison Diana Burcar and Rita Bennett It is certified that error appears in the above-identified patent and that said Letters Patent is hereby corrected as shown below:

At Column 4, Line 49, please delete "$d_{small}$," and add -- $d_{small}$ --.

At Column 5, Line 16, please delete "10," and insert -- 110, --.

Signed and Sealed this
Twenty-second Day of November, 2011

David J. Kappos
*Director of the United States Patent and Trademark Office*